United States Patent [19]

Long et al.

[11] Patent Number: 4,561,785
[45] Date of Patent: Dec. 31, 1985

[54] MODIFIED THROTTLING CALORIMETER

[75] Inventors: Stephen L. Long, Houston; Yin L. Cheung, Sugarland, both of Tex.

[73] Assignee: Texaco Inc., White Plains, N.Y.

[21] Appl. No.: 611,657

[22] Filed: May 18, 1984

[51] Int. Cl.$^4$ .............................................. G01K 17/12
[52] U.S. Cl. ...................................... 374/42; 364/571; 374/33
[58] Field of Search ................................. 374/42, 31

[56] References Cited

U.S. PATENT DOCUMENTS

| | | | |
|---|---|---|---|
| 401,111 | 4/1889 | Barrus | 374/42 |
| 465,321 | 12/1891 | Gehre | 374/42 |
| 3,363,460 | 1/1968 | Baumann | 374/42 |
| 3,453,880 | 7/1969 | Dropkin | 374/35 |
| 4,295,368 | 10/1981 | Jannone | 374/42 |
| 4,352,159 | 9/1982 | Colby | 364/571 X |

OTHER PUBLICATIONS

"Steam-Quality Determinations", Kents Mechanical Engineer's Handbook, Power Volume, 12th Edition, 1950, pp. 7-21, 7-22.

Primary Examiner—Daniel M. Yasich
Attorney, Agent, or Firm—Robert A. Kulason; James J. O'Loughlin; Robert B. Burns

[57] ABSTRACT

Method and apparatus for determining the quality of typical steam used in steam flooding for secondary recovery of petroleum, using a modification of the conventional throttling calorimeter based on thermodynamic properties of the steam. Automatic continuous operation with heat added thereto is also disclosed.

7 Claims, 4 Drawing Figures

MODIFIED THROTTLING CALORIMETER

BACKGROUND OF THE INVENTION

In the operation of steam flooding to stimulate production of oil from oil reservoirs it is important to have a simple and accurate method to determine the quality of steam at the well head of an injection well. In such a stimulation process the amount of heat input to the reservoir determines the rate and amount of oil recovery, and heat input depends directly upon the steam quality. Steam that is generated for injection into the reservoir arrives at the well head as saturated or wet steam, i.e., a mixture of vapor and liquid, at super-atmospheric pressure. The greater the proportion of vapor in that mixture, i.e., the greater the steam quality, the more the heat input to the reservoir. Steam quality thus directly affects the rate and the ultimate amount of recovery of oil, and therefore has a bearing upon earnings and investment requirements.

One conventional method of measuring steam quality is by collecting a sample of the liquid phase of the steam and comparing the salt concentration of the sample with that of the feedwater to the boiler. However this method cannot be used if steam is distributed by a manifold system. Another method is by using an orifice plate and relating the pressure drop to the quality by use of a correlation. This method is accurate only in certain pressure ranges and again cannot be used in a manifold system.

SUMMARY OF THE INVENTION

In this invention the quality of steam in a vessel or pipeline, such as used for delivering steam to wellheads for steam flooding to enhance the recovery of petroleum, is determined directly by using measurable thermodynamic properties of the steam. The method of this invention can be used in any configuration and in any pressure range, is based on a modification of the conventional throttling calorimeter, and, since it uses an energy balance to determine steam quality, is capable of greater accuracy than a method using a correlation. It is also adaptable to automatic continuous operation.

In this method a representative sample of the vessel or line steam is captured and passed through a throttling orifice as in the conventional throttling calorimeter. At this point however, since typical steam used in enhanced recovery operations is of such low quality that the expanded steam is still saturated or wet steam and therefore the throttling calorimeter equation is not applicable, the method of this invention departs from the throttling calorimeter method by introducing a measured amount of heat into the expanded steam sufficient to superheat the steam. Pressure and temperature measurements and a mass flow rate measurement are made, and an appropriately modified throttling calorimeter equation is used to obtain the quality of the steam in the vessel.

It is an object of this invention to obtain an accurate determination of the quality of steam when the quality is too low to be determined by a conventional throttling calorimeter.

A further object is to obtain a determination of the quality of steam by an energy balance and the use of thermodynamic properties of the steam.

A further object is to obtain a determination of the quality of steam by a method that can be used in any configuration and in any pressure range.

A further object is to obtain a determination of the quality of steam with an accuracy greater than can be achieved by any method using a correlation.

Another object is to obtain an automatic and continuous determination of the quality of steam.

Another object is to measure the mass flow rate of steam by an energy balance method.

BRIEF DESCRIPTION OF THE DRAWINGS

The foregoing and other objects and benefits of the invention will be more fully set forth below in connection with the best mode contemplated by the inventor of carrying out the invention, and in connection with which there are illustrations provided in the drawings, wherein.

DESCRIPTION OF THE PREFERRED EMBODIMENT

Figure 1:
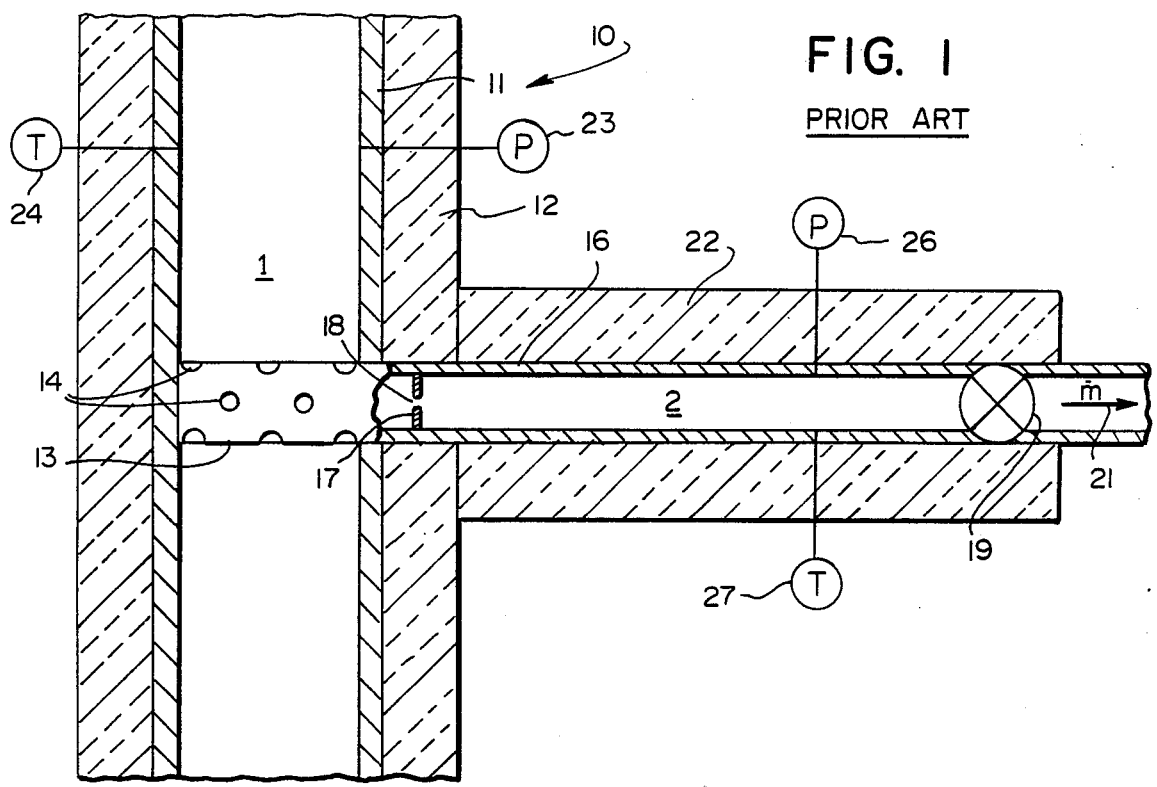
FIG. 1 is a schematic illustration of the prior art throttling calorimeter for determining steam quality.
Figure 2:
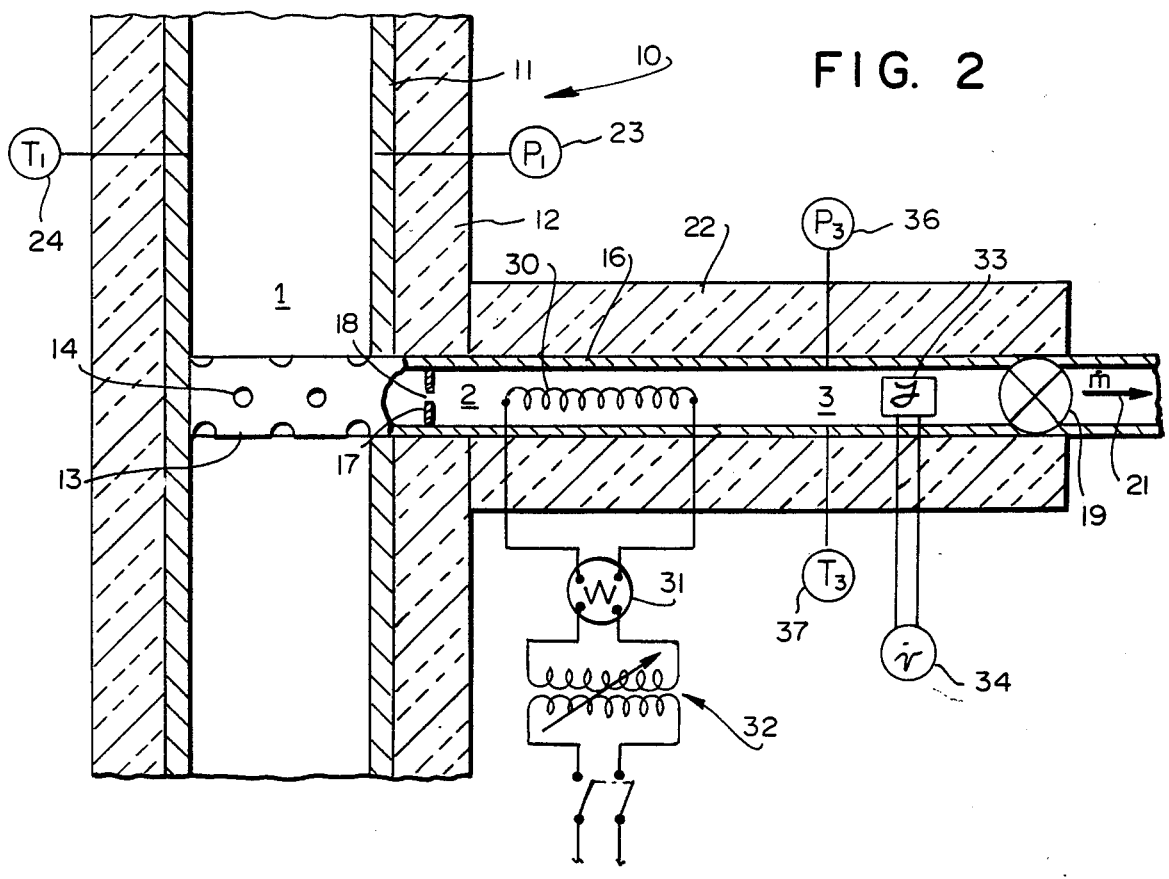
FIG. 2 is a schematic illustration of the modification of the throttling calorimeter according to this invention.

This invention is concerned with determining the quality, i.e. the mass ratio of vapor to vapor+liquid, of saturated steam contained within a vessel 10 (FIGS. 1 and 2). Vessel 10, which may be a steam pipe line, has walls 11 surrounded by thermal insulation 12.

Prior Art—Throttling Calorimeter

A prior art method of determining steam quality, known as the throttling calorimeter, is illustrated schematically in FIG. 1. A steam sampling probe 13 extends through wall 11 into vessel 10 and has openings 14 through which a steam sample, having quality substantially the same as the saturated steam contained within vessel 10, may be drawn off from vessel 10. Sampling probe 13 communicates with steam sample conduit 16, which is surrounded by thermal insulation 22 and contains a valve 19 and an orifice plate 17 having a throttling orifice 18. When valve 19 is opened a controlled amount, steam sample 21 flows at mass flow rate m from the region indicated by numeral 1 within vessel 10 through openings 14 in probe 13 along conduit 16 through throttling orifice 18 in orifice plate 17 into the region indicated by numeral 2 between orifice plate 17 and valve 19 within conduit 16, and thence through valve 19. Pressure measuring means 23 and temperature measuring means 24 are provided for measurements on steam in high pressure region 1, and pressure measuring means 26 and temperature measuring means 27 are provided for measurements on steam in low pressure region 2.

In the prior art throttling calorimeter method the quality of the region 1 steam is determined by the use of measurements made and equations derived as follows. When steam passes through a throttling orifice it undergoes an adiabatic expansion with no external work. Under those conditions the enthalpy before throttling is the same as the enthalpy after throttling. Thus in the throttling calorimeter of FIG. 1 the enthalpy $h_1$ for the high pressure region 1 steam and the enthalpy $h_2$ for the low pressure region 2 steam are equal.

$$h_1 = h_2 \tag{1}$$

If the region 1 steam has enthalpy greater than 1150.4 Btu/lbm and is throttled to near atmospheric pressure, the low pressure region 2 steam will be superheated, containing vapor only. The enthalpy of this superheated steam, $h_2$, can be readily determined from steam tables if the temperature and pressure are known. Knowing $h_2$ and the fact that $h_1 = h_2$, we also know $h_1$. The fact that $h_2$ is a function of the pressure and the temperature is written as $$h_2(P_2, T_2)$$

whence $h_{f1} = h_2(P_2, T_2)$ (2)

A useful relationship pertaining to saturated steam is that

| the enthalpy of saturated steam (such as $h_1$) containing both vapor and liquid phases | = | the enthalpy of the vapor phase ($h_{v1}$) times the steam quality ($X_1$) | + | the enthalpy of the liquid phase ($h_{f1}$) times one minus the steam quality $(1 - X_1)$ | expressed by the equation $$h_1 = X_1 h_{v1} + (1 - X_1) h_{f1}$$

which upon rearranging terms, substituting for $(h_{v1} - h_{f1})$ its equivalent, the enthalpy of vaporization $h_{fg1}$, and substituting for $h_1$ in equation (2), yields $$h_{f1} + X_1 h_{fg1} = h_2(P_2, T_2) \tag{3}$$

Equation (3) is solved for $X_1$, the steam quality in region 1:

$$X_1 = \frac{h_2(P_2, T_2) - h_{f1}}{h_{fg1}} \tag{4}$$

The above description pertains to the prior art device known as a throttling calorimeter. Generally for region 2 steam to be superheated, region 1 steam quality must be greater than 90%. In most steam flood projects for enhanced recovery of petroleum, however, the steam quality is less than 90%. Consequently the throttling calorimeter is not generally useful in steam flood projects.

Modified Throttling Calorimeter

The following description pertains to the modified throttling calorimeter of this invention, shown schematically in FIG. 2, in which many of the same elements as in FIG. 1 are repeated, with the same numeric designations. The modified throttling calorimeter is useful where the steam quality is less than 90% and therefore is useful in most steam flood projects. When such low quality region 1 steam is expanded through a throttling orifice the expanded region 2 steam is still saturated steam containing both liquid and vapor phases. The enthalpy of such two-phase region 2 steam cannot be determined from measurements of temperature and pressure as in the throttling calorimeter since it is not single phase steam and further since there is no way of knowing what proportion of the region 2 steam is liquid and what proportion vapor.

In this invention heat is added by electric heater 30 powered by variable transformer 32 at a rate measured by wattmeter 31 to steam sample 21 as it leaves region 2 (just downstream of orifice plate 17) and before it reaches region 3 (just upstream of valve 19). Pressure measuring means 36 and temperature measuring means 37 are provided for measurements on steam in region 3. Heat is added by heater 30 at a rate sufficient to gasify region 2 saturated steam and convert it to region 3 superheated steam. The power input to heater 30 is adjusted to achieve complete conversion to superheated steam. This adjustment is made by increasing the voltage applied to heater 30 by variable transformer 32 and observing the temperature in region 3 measured by means 37. If the temperature measured by means 37 stays constant while heat is being added at successive higher rates, it is an indication that there is still some liquid component present, and the steam is saturated or wet steam. When the temperature measured by means 37 thereafter rises upon an increase in the rate of addition of heat, it is an indication that the conversion to superheated steam is complete. The temperature $T_3$ and the pressure $P_3$ at that point are noted for use in the calculation of region 1 or vessel steam quality. A modified throttling calorimeter is the result of this procedure of adding heat, and an appropriately modified equation, derived below, can be used to determine the region 1 steam quality.

The rate at which heat is added through heater 30 to region 2 saturated steam is $(\dot{Q}_{in})_2$ as measured by wattmeter 31. There will be some heat loss $(\dot{Q}_{out})_2$ from the region 3 steam, despite the use of thermal insulation 22, and this rate of heat loss is determined by calibrating the system as follows: the system without a sample flowing is heated to the estimated working temperature, and the power required to hold that temperature is measured by wattmeter 31—that power is $(\dot{Q}_{out})_2$. Heat is thus added to region 2 saturated steam at a measured net rate $(\dot{Q}_{in})_2 - (\dot{Q}_{out})_2$, with the steam flowing at a mass flow rate $\dot{m}$, and equation (2) is modified to $$h_1 = h_3(P_3, T_3) - \frac{(\dot{Q}_{in})_2 - (\dot{Q}_{out})_2}{\dot{m}} \tag{5}$$

where $h_3(P_3, T_3)$ is the enthalpy from steam tables of region 3 superheated steam at pressure $P_3$ and temperature $T_3$ after addition of heat to the sample.

Upon substitution again for $h_1$ as above, equation (5) becomes $$h_{f1} + X_1 h_{fg1} = h_3(P_3, T_3) - \frac{(\dot{Q}_{in})_2 - (\dot{Q}_{out})_2}{\dot{m}} \tag{6}$$

which can be solved for the desired region 1 or vessel steam quality $X_1$ $$X_1 = \frac{1}{h_{fg1}} \left( h_3 - h_{f1} - \frac{(\dot{Q}_{in})_2 - (\dot{Q}_{out})_2}{\dot{m}} \right) \tag{7}$$

where $h_{fg1}$ and $h_{f1}$ are obtained from steam tables, knowing either $P_1$ or $T_1$, and $h_3$ is obtained from steam tables knowing both $P_3$ and $T_3$. The quantity $\dot{m}$ can be obtained in any of several ways, for example by condensing sample 21 to the liquid phase as it issues from valve 19, collecting it and measuring the collected mass of liquid versus time. Another way is by use of a conventional single phase volumetric flow meter such as an orifice meter or the turbine meter 33 (FIG. 2) for measuring flow with associated volume flow rate indicator 34, and converting volume flow rate $\dot{v}$ to mass flow rate $\dot{m}$ by use of the single phase vapor density $d_3$ from steam tables for the known pressure and temperature. In other words $\dot{m} = \dot{v} d_3$.

Figure 3:
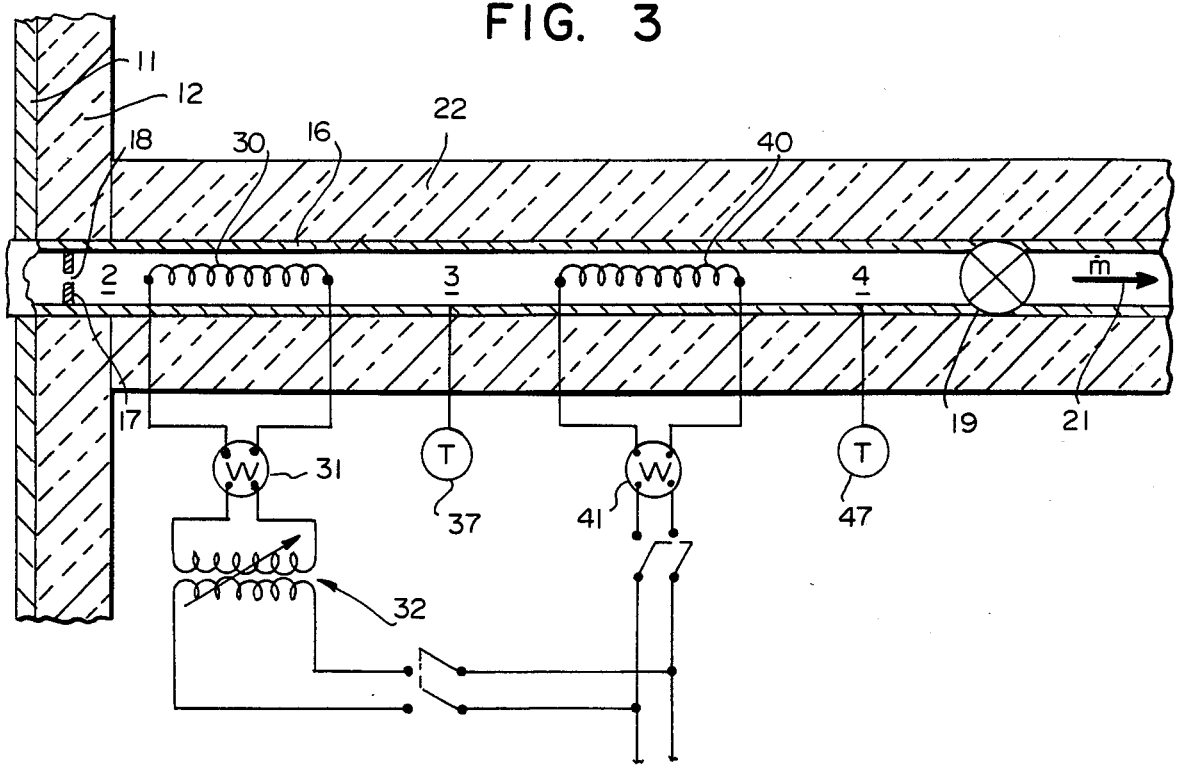
FIG. 3 is a schematic illustration of means for measuring mass flow by use of an energy balance.

Still another way to obtain $\dot{m}$ is by employing a second heater 40 (FIG. 3) and wattmeter 41 downstream of heater 30 and wattmeter 31 to add heat and measure net added heat to region 3 steam. Steam downstream of second heater 40 is region 4 steam, with provision of temperature measuring means 47 therefor. The net added heat rate supplied by heater 40 is $(\dot{Q}_{in})_3 - (\dot{Q}_{out})_3$, which is measured in the same way as $(\dot{Q}_{in})_2 - (\dot{Q}_{out})_2$ above. By equating this net heat addition rate to the increase in sensible heat, or $\dot{m}c_p(T_4 - T_3)$, where $(T_4 - T_3)$ is the difference between temperature in region 4 and temperature in region 3, and $c_p$ is the specific heat at constant pressure, from tables, one can determine $\dot{m}$ by the equation $$\dot{m} = \frac{(\dot{Q}_{in})_3 - (\dot{Q}_{out})_3}{c_p(T_4 - T_3)} \tag{8}$$

Thus by performing the steps of this invention, measuring the quantities as above set forth, and using the above equations one can obtain the quality of typical steam used in steam flooding for secondary recovery of petroleum in terms of thermodynamic properties.

Automatic Continuous Measurement

Figure 4:
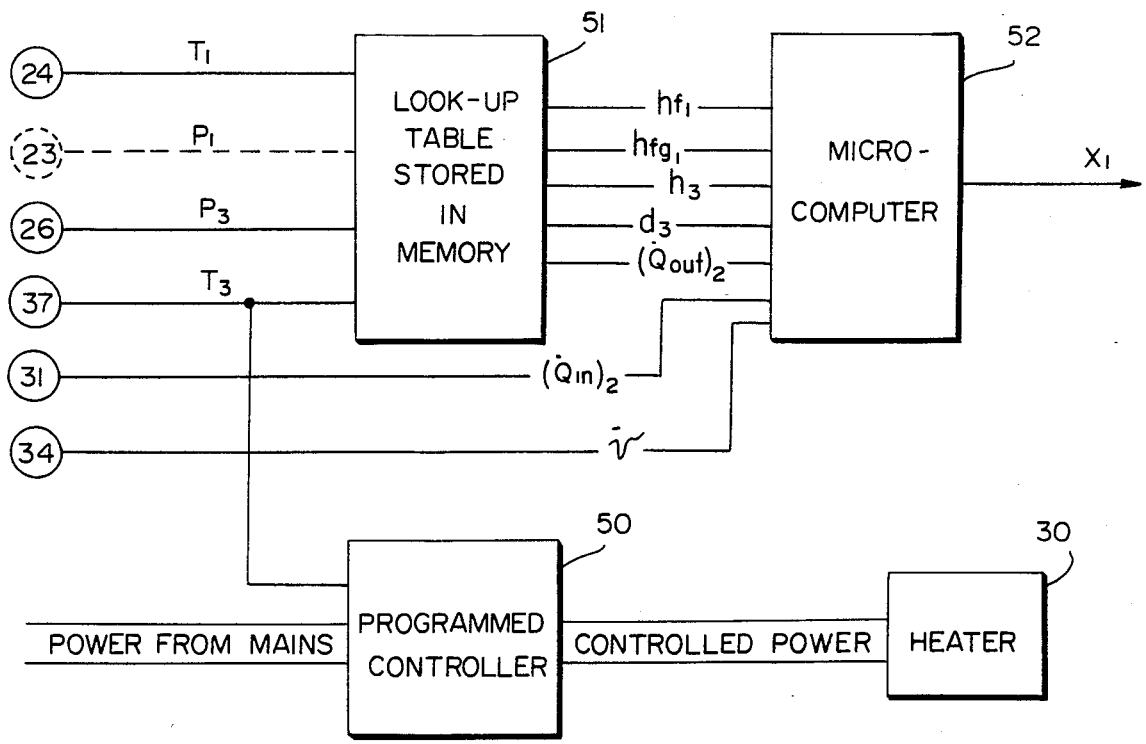
FIG. 4 is a flow diagram illustrating how the data obtained according to this invention can be processed to provide an automatic continuous read-out of steam quality.

The quality of the steam within vessel 10 can also be measured automatically and continuously by use of the data processing procedure shown schematically in FIG. 4. Valve 19 (FIG. 2) is opened a controlled amount, and a steady state is reached with sample 21 flowing at mass flow rate $\dot{m}$ through conduit 16. Heater 30 is operated continuously at a power level that provides complete conversion of the steam to superheated steam. This power level is determined by programmed controller 50 (FIG. 4), which is programmed to make periodic trial increases in the power level of heater 30, each increase being followed a suitable interval later by a measurement of temperature $T_3$, and to seek and hold a power level for which the temperature vs power characteristic indicates complete conversion to superheated steam. As explained above, this power level is any one which is greater than the levels at which power increments result in no increase in temperature $T_3$.

A "look-up table" stored in memory 51 contains all values needed for solving equation (7). Independent variables stored in 51 include practical ranges of values for $T_1$ from temperature measuring means 24, values for $P_3$ from pressure measuring means 26, and values for $T_3$ from temperature measuring means 37. As an alternative to $T_1$ values, $P_1$ values from means 23 might be stored, as indicated by the dashed line in FIG. 4—only one of $T_1$ and $P_1$ is required. Outputs from look-up table 51 for inputting to microcomputer 52 include dependent variable values for $h_{f1}$ and $h_{fg1}$ from steam table values corresponding to $T_1$ (or $P_1$), also $h_3$ and $d_3$ from steam table values corresponding to $T_3$ and $P_3$. Also stored in look-up table 51 are experimentally determined calibration values $(\dot{Q}_{out})_2$ corresponding to a range of practical values for $T_3$. Additional inputs to microcomputer 52 include running values observed for $(\dot{Q}_{in})_2$ from wattmeter 31 and $\dot{v}$ from volume flow rate indicator 34. Microcomputer 52 operates continuously on the seven inputs fed into it to solve equation (7) and to provide a continuous determination of vessel steam quality $X_1$.

While we have chosen to illustrate and describe certain preferred embodiments of our invention, this is not to be considered as limiting but as illustrative only.

Therefore, what is claimed as new and is desired to be secured by letters patent is:

1. Apparatus for obtaining a measure of the quality of saturated steam which occupies a vessel, said steam having liquid and vapor components, comprising
   (1) means for drawing from said vessel at a constant mass flow rate through a throttling orifice a flowing sample of said steam,
   (2) means for adding heat to said flowing throttled sample of steam at a rate sufficient to gasify completely said flowing throttled sample of steam,
   (3) means for measuring the net rate at which heat is added to said flowing throttled sample of steam,
   (4) means for measuring said mass flow rate of said flowing sample of steam,
   (5) means for measuring one of the temperature and the pressure of said saturated steam in said vessel,
   (6) means for measuring the temperature of said heated flowing throttled sample of steam, and
   (7) means for measuring the pressure of said heated flowing throttled sample of steam, such that a measure of the quality of said saturated steam in said vessel can be obtained by the equation $$X_1 = \frac{1}{h_{fg1}} \left( h_3 - h_{f1} - \frac{(\dot{Q}_{in})_2 - (\dot{Q}_{out})_2}{\dot{m}} \right)$$

where $X_1$ is a measure of the quality of said saturated steam in said vessel,
$(\dot{Q}_{in})_2 - (\dot{Q}_{out})_2$ is the net rate of heat addition measured by the means of step (3),
$\dot{m}$ is the mass flow rate measured by the means of step (4),
$h_{fg1}$ is the enthalpy of vaporization of steam in said vessel as obtained from steam tables for one of the temperature and pressure measured by the means of step (5),
$h_3$ is the enthalpy of said heated flowing sample of steam as obtained from steam tables for the temperature measured by the means of step (6) and the pressure measured by the means of step (7),
and $h_{f1}$ is the enthalpy of the liquid phase of steam in said vessel as obtained from steam tables for one of the temperature and pressure measured by the means of step (5).

2. Apparatus for obtaining a measure of the quality of saturated steam which occupies a vessel, said steam having liquid and vapor components, comprising
   (1) means for drawing from said vessel at a constant mass flow rate a flowing sample of steam having substantially the same quality as said saturated steam in said vessel,
   (2) means for throttling said flowing sample of steam, (3) means for adding heat to said flowing throttled sample of steam at a rate sufficient to gasify completely said flowing throttled sample of steam,
(4) means for measuring said rate at which heat is added,
(5) means for measuring the rate at which heat is lost from said heated flowing throttled sample of steam,
(6) means for measuring said mass flow rate of said flowing sample of steam,
(7) means for measuring one of the temperature and the pressure of said saturated steam in said vessel,
(8) means for measuring the temperature of said heated flowing throttled sample of steam, and
(9) means for measuring the pressure of said heated flowing throttled sample of steam,
(10) such that a measure of the quality of said saturated steam in said vessel can be obtained by the equation $$X_1 = \frac{1}{h_{fg1}} \left( h_3 - h_{f1} - \frac{(\dot{Q}_{in})_2 - (\dot{Q}_{out})_2}{\dot{m}} \right)$$

where $X_1$ is a measure of the quality of said saturated steam in said vessel,
$(\dot{Q}_{in})_2$ is the rate of heat addition measured by the means of step (4),
$(\dot{Q}_{out})_2$ is the rate of heat loss measured by the means of step (5),
$\dot{m}$ is the mass flow rate measured by the means of step (6),
$h_{fg1}$ is the enthalpy of vaporization of steam in said vessel as obtained from steam tables for one of the temperature and pressure measured by the means of step (7),
$h_3$ is the enthalpy of said heated flowing sample of steam as obtained from steam tables for the temperature measured by the means of step (8) and the pressure measured by the means of step (9),
and $h_{f1}$ is the enthalpy of the liquid phase of steam in said vessel as obtained from steam tables for one of the temperature and pressure measured by the means of step (7).

3. A method for automatically and continuously obtaining a measure of the quality of saturated steam which occupies a vessel, comprising the steps of
(1) drawing from said vessel at a constant mass flow rate a flowing sample of steam having substantially the same quality as said saturated steam in said vessel,
(2) throttling said flowing sample of steam,
(3) adding heat to said flowing throttled sample of steam at a controlled rate sufficient to gasify completely said flowing throttled sample of steam,
(4) measuring said controlled rate at which heat is added,
(5) measuring the rate at which heat is lost from said heated flowing throttled sample of steam,
(6) measuring parameters from which said mass flow rate can be determined,
(7) measuring one of the temperature and the pressure of said saturated steam in said vessel,
(8) measuring the temperature of said heated flowing throttled sample of steam,
(9) measuring the pressure of said heated flowing throttled sample of steam, and
(10) continuously obtaining a measure of the quality of said saturated steam in said vessel by means of a microcomputer programmed to solve the equation $$X_1 = \frac{1}{h_{fg1}} \left( h_3 - h_{f1} - \frac{(\dot{Q}_{in})_2 - (\dot{Q}_{out})_2}{\dot{m}} \right)$$

where $X_1$ is a measure of the quality of said saturated steam in said vessel,
$(\dot{Q}_{in})_2$ is the controlled rate of heat addition measured in step (4),
$(\dot{Q}_{out})_2$ is the rate of heat loss measured in step (5),
$\dot{m}$ is the mass flow rate determined from the parameters measured in step (6),
$h_{fg1}$ is the enthalpy of vaporization of steam in said vessel as obtained from steam tables for one of the temperature and pressure measured in step (7),
$h_3$ is the enthalpy of said heated flowing sample of steam as obtained from steam tables for the temperature measured in step (8) and the pressure measured in step (9),
and $h_{f1}$ is the enthalpy of the liquid phase of steam in said vessel as obtained from steam tables for one of the temperature and pressure measured in step (7).

4. A method for obtaining a measure of the quality of saturated steam which occupies a vessel, comprising the steps of
(1) drawing from said vessel at a constant mass flow rate a flowing sample of steam having substantially the same quality as said saturated steam in said vessel,
(2) throttling said flowing sample of steam,
(3) adding heat to said flowing throttled sample of steam at a rate sufficient to gasify completely said flowing throttled sample of steam,
(4) measuring said rate at which heat is added,
(5) measuring the rate at which heat is lost from said heated flowing throttled sample of steam,
(6) measuring said mass flow rate of said heated flowing throttled sample of steam,
(7) measuring one of the temperature and the pressure of said saturated steam in said vessel,
(8) measuring the temperature of said heated flowing throttled sample of steam,
(9) measuring the pressure of said heated flowing throttled sample of steam, and
(10) obtaining a measure of the quality of said saturated steam in said vessel by the equation $$X_1 = \frac{1}{h_{fg1}} \left( h_3 - h_{f1} - \frac{(\dot{Q}_{in})_2 - (\dot{Q}_{out})_2}{\dot{m}} \right)$$

where $X_1$ is a measure of the quality of said saturated steam in said vessel,
$(\dot{Q}_{in})_2$ is the rate of heat addition measured in step (4),
$(\dot{Q}_{out})_2$ is the rate of heat loss measured in step (5),
$\dot{m}$ is the mass flow rate measured in step (6),
$h_{fg1}$ is the enthalpy of vaporization of steam in said vessel as obtained from steam tables for one of the temperature and pressure measured in step (7),
$h_3$ is the enthalpy of said heated flowing sample of steam as obtained from steam tables for the temperature measured in step (8) and the pressure measured in step (9), and $h_{fl}$ is the enthalpy of the liquid phase of steam in said vessel as obtained from steam tables for one of the temperature and pressure measured in step (7).

5. The method of claim 4 wherein said step of measuring the mass flow rate of said heated flowing throttled steam comprises
   (1) adding additional heat to said heated flowing throttled sample of steam,
   (2) measuring said rate at which said additional heat is added,
   (3) measuring the rate at which heat is lost from said additionally heated flowing throttled sample of steam,
   (4) measuring the temperature difference between said additionally heated flowing throttled sample of steam and said heated flowing throttled sample of steam, and
   (5) determining said mass flow rate of flowing steam by an equation relating said mass flow rate to measurements made in steps (2), (3), and (4).

6. The method of claim 4 wherein said step of measuring the mass flow rate of said heated flowing throttled steam comprises
   measuring the volume flow rate of said steam,
   determining from steam tables the density of said heated flowing throttled steam as a function of said measurements of the temperature and pressure thereof, and
   determining the mass flow rate from the product of said volume flow rate and said density.

7. A method for obtaining a measure of the quality of saturated steam which occupies a vessel, comprising the steps of
   (1) drawing from said vessel at a constant mass flow rate through a throttling orifice a flowing sample of said steam,
   (2) adding heat to said flowing throttled sample of steam at a rate sufficient to gasify completely said flowing throttled sample of steam,
   (3) measuring the net rate at which heat is added to said flowing throttled sample of steam,
   (4) measuring said mass flow rate of said flowing sample of steam,
   (5) measuring one of the temperature and pressure of said saturated steam in said vessel,
   (6) measuring the temperature and pressure of said heated flowing throttled sample of steam, and
   (7) obtaining a measure of the quality of said saturated steam in said vessel by the equation $$X_1 = \frac{1}{h_{fg1}} \left( h_3 - h_{fl} - \frac{(\dot{Q}_{in})_2 - (\dot{Q}_{out})_2}{\dot{m}} \right)$$

where $X_1$ is a measure of the quality of said saturated steam in said vessel,
$(\dot{Q}_{in})_2 - (\dot{Q}_{out})_2$ is the net rate of heat addition measured in step (3),
$\dot{m}$ is the mass flow rate measured in step (4),
$h_{fg1}$ is the enthalpy of vaporization of steam in said vessel as obtained from steam tables for one of the temperature and pressure measured in step (5),
$h_3$ is the enthalpy of said heated flowing sample of steam as obtained from steam tables for the temperature and pressure measured in step (6),
and $h_{fl}$ is the enthalpy of the liquid phase of steam in said vessel as obtained from steam tables for one of the temperature and pressure measured in step (5).

* * * * *